(12) United States Patent
Wu et al.

(10) Patent No.: US 7,939,703 B2
(45) Date of Patent: May 10, 2011

(54) METHOD FOR PHOTOCATALYTIC ISOMERIZATION OF 1,2-DIPHENYLETHYLENE ANALOGUES

(75) Inventors: Li-Zhu Wu, Beijing (CN); Ming-Li Peng, Beijing (CN); Li Zhou, Beijing (CN); Deng-Hui Wang, Beijing (CN)

(73) Assignee: Technical Institute of Physics and Chemistry of Chinese Academy of Science, Beijing (CN)

( * ) Notice: Subject to any disclaimer, the term of this patent is extended or adjusted under 35 U.S.C. 154(b) by 366 days.

(21) Appl. No.: 12/327,596

(22) Filed: Dec. 3, 2008

(65) Prior Publication Data
US 2009/0156872 A1    Jun. 18, 2009

(30) Foreign Application Priority Data
Dec. 3, 2007 (CN) .......................... 2007 1 0178634

(51) Int. Cl.
*C07C 5/23* (2006.01)
(52) U.S. Cl. ......... 585/664; 585/665; 585/670; 585/671
(58) Field of Classification Search .................. None
See application file for complete search history.

(56) References Cited

U.S. PATENT DOCUMENTS
5,525,632 A    6/1996    Obsumi et al.

FOREIGN PATENT DOCUMENTS
CN    1723884    1/2006

OTHER PUBLICATIONS

Olson, A. R., "The Study of Chemical Reactions From Potential Energy Diagrams," Trans. Faraday Soc., 1931, 27 69-76.
Saltiel et al., "Mechanisms of Photochemical Reactions in Solution. IVII. cis-trans Isomerization of the Stilbenes by Excitation Transfer from Low Energy Sensitizers," J. Am. Chem. Soc., 85 (1963) 2515-2516.
Hammond et al., "Mechanisms of Photochemical Reactions in Solution. XXII. Photochemical cis-trans Isomerization," J. Am. Chem. Soc. (1964) 86, 3197-3217.
Saltiel, J., "Perdueteriostibene. he Role of Phantom States in the cis-trans Photoisomerization of Stilbenes," J. Am. Chem. Soc. (1967) 89:4, 1036-1037.
Caldwell et al., "Fluorenone-Photosensitized Isomerization of trans-Stilbene. Inefficiencies both in Intersystem Crossing and in Triplet Excitation Transfer," J. Am. Chem. Soc. (1971) 93:2, 532-534.

Valentine et al., "Mechanisms of Photochemcial Reactions in Solution. LXVII. energy Wastage in Photosensitized Isomerizations of the Stilbenes," J. Am. Chem. Soc. (1972) 94:10, 3449-3454.
Saltiel et al., "Mechanism of direct cis-trans photoisomerization of the stilbenes. Solvent viscosity and the azulene effect," J. Am. Chem. Soc.(1972) 94:8 2742-2749.
Liu, R. S. H., "9,10-Dichloroanthracene-Sensitized Isomerization of Stilbenes. The Question of Energy Transfer between Intimately Associated Molecular Pairs," J. Am. Chem. Soc. (1968) 90:7, 1899-1900.
Saltiel, J., "Perdeuteriostilbene. The Triplet and Singlet Paths for Stilbene Photoisomerization," J. Am. Chem. Soc. (1968) 90:23, 6394-6400.
Saltiel et al., "Nonvertical Triplet Excitation Transfer to cis- and trans-Stilbene," J. Am. Chem. Soc. (1984) 106, 3144-3151.
Whitten et al., "Photochemistry of Metalloporphyrin Complexes. Ligand Photoisomerization via Intramolecular Energy Transfer," J. Am. Chem. Soc. (1972) 94:22, 7811-7823.
Zarnegar et al., "Photoreactions of Transition Metal Complexes. Ligand Reactivity as a Probe for Excited-State Characterization," J. Am. Chem. Soc. (1973) 95:13, 4367-4372.
Mercer-Smith et al., "Photosensitization of Stilbene Isomerization by Palladium and Platinum Porphyrins, an Intermolecular Quantum Chain Process," J. Am. Chem. Soc. (1978) 100:9, 2620-2625.
Ams et al., "Intramolecularly Sensitized Precipitons: A Model System for Application to Metal Sequestration," J. Am. Chem. Soc. (2006) 128, 250-256.
Ams et al., "Benzil-Tethered Precipitons for Controlling Solubility: A Round-Trip Energy-Transfer Mechanism in the Isomerization of Extended Stilbene Analogues," J. Am. Chem. Soc. (2007) 129, 3966-3972.
Eenkhoorn et al., "The Wittig Reaction of Indol-2-methyltriphenylphosphonium Iodide with 4-Piperidone Derivatives and Aromatic Aldehydes," Can. J. Chem. vol. 51 (1973) 792-810.
Lewis et al., "Molecular Structure and Photochemistry of (E)- and (Z)-2-(2-(2-Pyridyl)ethenyl)indole. A Case of Hydrogen Bond Dependent One-Way Photoisomerization," J. Am. Chem. Soc. (1995) 117:11, 3029-3036.
Arai et al., ""One-Way" Photoisomerization Between cis- and trans-Olefin. A Novel Adiabatic Process in the Excited State," Tetrahedron Letters, vol. 24, No. 28, (1983) 2873-2876.

*Primary Examiner* — Tam M Nguyen
(74) *Attorney, Agent, or Firm* — Volpe and Koenig, P.C.

(57) ABSTRACT

The present invention relates to methods for accelerating the trans-cis isomerization of 1,2-diphenylethylene analogues by using photocatalyst. According to this invention, in the presence of polypyridyl platinum(II) complex with catalytic dosage, a solution containing trans-1,2-diphenylethylene analogues or mixture of cis- and trans-1,2-diphenylethylene analogues is irradiated by visible light to prepare product of cis-1,2-diphenylethylene analogues or product predominantly being cis-1,2-diphenylethylene analogues under inert gas atmosphere. This method has the advantages of fast reaction, high performance, easy separation of reaction system and recycle of the polypyridyl platinum (II) complexes.

8 Claims, 1 Drawing Sheet

METHOD FOR PHOTOCATALYTIC ISOMERIZATION OF 1,2-DIPHENYLETHYLENE ANALOGUES

FIELD OF THE INVENTION

The present invention relates to methods for accelerating the trans-cis isomerization of 1,2-diphenylethylene analogues by using photocatalyst. According to this invention, in the presence of polypyridyl platinum(II) complex with catalytic dosage, a solution containing trans-1,2-diphenylethylene analogues or mixture of cis- and trans-1,2-diphenylethylene analogues is irradiated by visible light to prepare product of cis-1,2-diphenylethylene analogues or product predominantly being cis-1,2-diphenylethylene analogues under inert gas atmosphere.

BACKGROUND OF THE INVENTION

There are two kinds of isomers, cis- and trans-isomers of 1,2-diphenylethylene analogues. Because the cis-isomer has higher energy than that of the trans-isomer, 1,2-diphenylethylene analogues normally exists in the form of trans-isomer with a more stable configuration. In general, the synthetic routes of 1,2-diphenylethylene analogues are Wittig reaction or modified Wittig reactions, condensation between carbon anion and hydrazone obtained from aromatic aldehydes, reductive coupling of carbonyl compound or self-coupling of alpha-lithiumbenzylphenylsulfone to prepare trans-isomer of 1,2-diphenylethylene analogues predominantly rather than the cis-isomer. However, the cis-1,2-diphenylethylene analogues is different from the trans ones in both physical and chemical properties. As the U.S. Pat. No. 5,525,632 disclosed, the combrestatin with the structure of cis-1,2-diphenylethylene analogues has carcinostatics activity. And the Chinese patent CN1732884A reported that cis-1,2-diphenylethylene analogues can be used to prevent and to treat diabetes. Therefore, it is important to develop a method for the production of cis-1,2-diphenylethylene analogues.

The isomerization occurs between the two isomers under direct irradiation of lights. Hammond, G., and Satiel, J. reported that, when the singlet 1,2-diphenylethylene reaches reaction equilibrium under irradiation with ultraviolet light, the ratio of cis- to trans-isomers on the photostationary state is dependent on the different molar extinction coefficient of the isomers under the light wavelength used (J. Am. Chem. Soc. 1964, 86, 3197; J. Am. Chem. Soc. 1967, 89, 1036; J. Am. Chem. Soc. 1972, 94, 2742). Nevertheless, the quantum yield of the reaction is very low. Then they used the small molecules like benzophenone as photosensitizers to sensitize the trans-1,2-diphenylethylene to its triplet state, followed by isomerization to its cis-isomer. On the photostationary state, the ratio of cis- to trans-isomers is dependent on the triplet energy of the sensitizer used (J. Am. Chem. Soc. 1963, 85, 2515; J. Am. Chem. Soc. 1968, 90, 1899; J. Am. Chem. Soc. 1968, 90, 6394; J. Am. Chem. Soc. 1972, 94, 3449; J. Am. Chem. Soc. 1984, 106, 3144; J. Am. Chem. Soc. 1971, 93, 532). However, the short lifetime of the sensitizer and weak interaction between the sensitizer in excited state and the 1,2-diphenylethylene, together with the sensitizer bleaching during the reaction lead to low quantum yield of sensitization, long reaction time and complicated reaction products. To facilitate the photoisomerization, Whitten, D. G., et al introduced metalloporphyrin complexes such as zinc porphyrin and bipyridyl ruthenium complexes as sensitizers to reach the trans-isomer predominantly with high rate acceleration. (J. Am. Chem. Soc. 1972, 94, 7811; J. Am. Chem. Soc. 1973, 95, 4367; J. Am. Chem. Soc. 1978, 100, 2620). Recently Wilcox et al. covalently linked $[Ru(bpy)_3]^{2+}$ or benzil and 1,2-bis(biphenyl)ethene units to investigate the photoisomerization kinetics and found that the linked sensitizer increases the rate of isomerization and significantly changes the photostationary state (J. Am. Chem. Soc. 2006, 128, 250; J. Am. Chem. Soc. 2007, 129, 3966). Under specific condition, 1,2-diphenylethylene analogues can undergo one-way isomerization upon irradiation with light. Eenkhoorn et al. found that the one-way isomerization from trans-isomer to cis-isomer of singlet 1-(2-pyrrolyl)-2-(2-indolyl)ethene occurred (Can. J. Chem. 1973, 51, 792.). Lewis et al. also illustrated that the one-way isomerization is due to the existence of intramolecular hydrogen bond in ground state of the cis-isomer (J. Am. Chem. Soc. 1995, 117, 3029). In 1983 Arai, Tokumaru et al. reported that the triplet olefin substituted by styrylanthracene underwent one-way isomerization from cis-isomer to trans-isomer (Tetrahedron Lett. 1983, 24, 2873).

Taken all together, it is evident that there has been a great effort to study the isomerization of 1,2-diphenylethylene analogues since the first report of isomerization of olefin in 1931 (Trans. Faraday Soc., 1931, 27, 69). Despite of this, examples related to the preparation of cis-1,2-diphenylethylene analogues are quite few. In the present invention polypyridyl platinum (II) complexes are adopted as a highly effective photocatalyst, to accelerate the trans-cis photoisomerization of 1,2-diphenylethylene analogues by using visible light, to achieve the cis-1,2-diphenylethylene analogues or cis-1,2-diphenylethylene analogues predominantly at photostationary state.

SUMMARY OF THE INVENTION

The object of this invention is to provide a highly efficient method for photocatalytic isomerzation of 1,2-diphenylethylene analogues with the advantages of the formation of cis-1,2-diphenylethylene analogues or cis-1,2-diphenylethylene analogues predominantly at photostationary state, catalytic dosage of the complexes, utility of visible light, fast reaction and recycle of the catalyst.

DETAILED DESCRIPTION OF THE INVENTION

Figure 1:
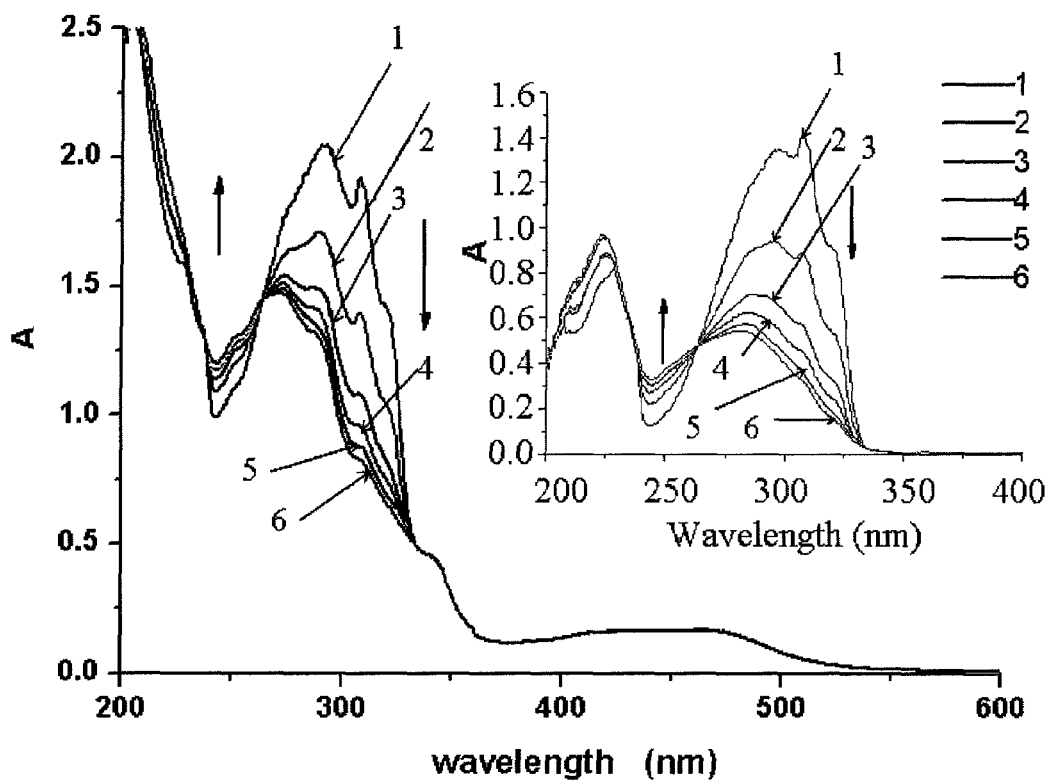
FIG. 1 shows the UV-vis absorption spectrum of the solution containing trans-1,2-diphenylethylene (wherein $R_1$ is phenyl, $R_2$ is phenyl) and 2,2':6',2''-terpyridyl platinum(II) complex (wherein $R_3$ is $C_6H_4OCH_3$-4, $R_4$ is $C\equiv CC_6H_4C\equiv CC_6H_5$-4, $R_5$ and $R_6$ are H independently) in acetonitrile, irradiated by light ($\lambda$>400 nm) in example 1. The total reaction time was 10 min. The inserted spectrum is the subtractive spectrum and the vertical arrow means the direction of spectral changes with time. The irradiation time for curves 1~6 are 0, 20, 40, 60, 90, 150 seconds, respectively.

The method provided in this invention includes that, in the presence of polypyridyl platinum(II) complex with catalytic dosage, a solution containing trans-1,2-diphenylethylene analogues or mixture of cis- and trans-1,2-diphenylethylene analogues is irradiated by visible light under inert gas (such as, nitrogen or argon) atmosphere to prepare product of cis-1,2-diphenylethylene analogues or product predominantly being cis-1,2-diphenylethylene analogues.

The reaction route of this invention is:

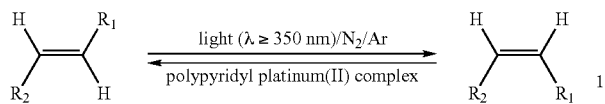

The process for the method provided in this invention comprises:

1. Dissolving polypyridyl platinum (II) complex and trans-1,2-diphenylethylene analogue or mixture of trans- and cis-1,2-diphenylethylene analogues into organic solvent (such as one or more selected from the group consisting of acetonitrile, dichloromethane, benzene, and toluene) to make the reaction solution.

2. Under inert gas (such as, nitrogen or argon) atmosphere, the reaction solution obtained from step 1 is irradiated by visible light and monitored by gas chromatography (GC) or UV-vis spectroscopy, wherein the wavelength is about 350 nm or longer, more preferably from about 350 nm to about 600 nm. The reaction time is dependent on the concentration and volume of reaction solutions. At the end of the reaction cis-1,2-diphenylethylene analogue or cis-1,2-diphenylethylene analogue as a predominant product is prepared.

In step 1, the concentration of the trans-1,2-diphenylethylene analogues or mixture of cis- and trans-1,2-diphenylethylene analogues contained in the reaction solution is from dilute to its saturated solution in the organic solvent, for example, from $10^{-5}$ mol/L to saturation. And the preferred concentration of polypyridyl platinum(II) complex is from about $10^{-7}$ mol/L to saturated, more preferably, from $10^{-7}$ mol/L to about $10^{-3}$ mol/L.

The cis- and trans-1,2-diphenylethylene analogues involved in this invention respectively have the following structure represented by Formula I:

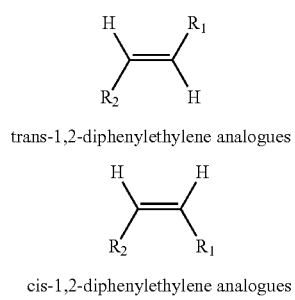

wherein in Formula I, $R_1$ is phenyl, and $R_2$ is phenyl, 2-pyridyl, 3-pyridyl, 4-pyridyl, 2-furyl, 4-methylphenyl, 4-methoxylphenyl or 4-nitrophenyl; or $R_1$ is 2-thienyl, and $R_2$ is 2-thienyl, phenyl, 4-methylphenyl, or 4-methoxylphenyl; or $R_1$ is 3-thienyl, and $R_2$ is phenyl, 4-methylphenyl, or 4-methoxylphenyl; or $R_1$ is 2-pyridyl, and $R_2$ is 2-pyridyl, 4-pyridyl, 4-methylphenyl, 4-methoxylphenyl or 2-naphthyl; or $R_1$ is 4-pyridyl, and $R_2$ is 4-pyridyl, 4-methylphenyl, 4-methoxylphenyl or 2-naphthyl; or $R_1$ and $R_2$ each are independently selected from 4-methylphenyl and 4-methoxylphenyl.

The catalyst involved in this invention is polypyridyl platinum(II) complex, including 2,2':6',2"-terpyridyl platinum(II) complex, 6-phenyl-2,2'-bipyridyl platinum(II) complex, 2,2'-bipyridyl platinum(II) complex, or phenanthroline platinum (II) complex.

Wherein said 2,2':6',2"-terpyridyl platinum(II) complex has the following structure represented by Formula II:

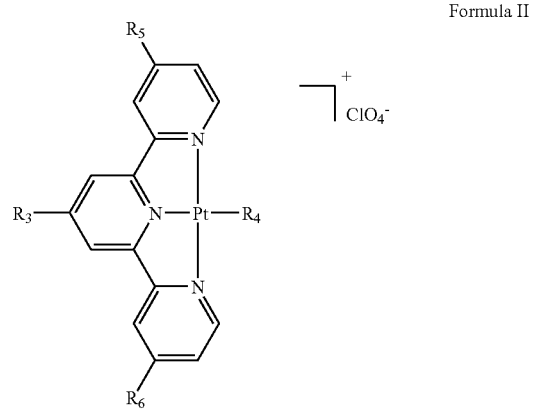

Wherein in Formula II, $R_3$ is $C_6H_4OCH_3$-4, $R_4$ is $C\equiv CC_6H_4C\equiv CC_6H_5$-4, $R_5$ and $R_6$ are H independently; or $R_3$ is $C_6H_4OCH_3$-4, $R_4$ is Cl, $R_5$ and $R_6$ are H independently; or $R_3$ is $C_6H_4CH_3$-4, $R_4$ is $C\equiv CC_6H_4C\equiv CC_6H_5$-4, $R_5$, $R_6$ are H independently; or $R_3$ is $C_6H_4CH_3$-4, $R_4$ is Cl, $R_5$ and $R_6$ are H independently; or $R_3$ is $C_6H_4CH_3$-4, $R_4$ is $C\equiv CC_6H_4CH_3$-4, $R_5$ and $R_6$ are H independently; or $R_3$ is $C_6H_4CH_3$-4, $R_4$ is $C\equiv CCH_2OH$, $R_5$ and $R_6$ are H independently; or $R_3$ is $C(CH_3)_3$, $R_4$ is $C\equiv CC_6H_5$, $R_5$ and $R_6$ are H independently; or $R_3$ is $C(CH_3)_3$, $R_4$ is Cl, $R_5$ and $R_6$ are H independently; or $R_3$ is $C_6H_4CH_3$-4, $R_4$ is $C\equiv CC_6H_5$, $R_5$ and $R_6$ are H independently; or $R_3$ is $C_6H_4CH_3$-4, $R_4$ is $C\equiv CC_6H_4OCH_3$-4, $R_5$ and $R_6$ are H independently; or $R_3$ is $C_6H_4CH_3$-4, $R_4$ is $C\equiv CC_6H_4Cl$-4, $R_5$ and $R_6$ are H independently; or $R_3$ is $C_6H_4CH_3$-4, $R_4$ is $C\equiv CC_6H_4OCOCH_3$, $R_5$ and $R_6$ are H independently; or $R_3$ is $C_6H_4CH_3$-4, $R_4$ is $C\equiv CSi(CH_3)_3$, $R_5$ and $R_6$ are H independently; or $R_3$ is $C_6H_4CH_3$-4, $R_4$ is $C\equiv C(CH_2)_nCH_3$ (n being an integer from 1 to 16), $R_5$ and $R_6$ are H independently; or $R_3$ is H, $R_4$ is $C\equiv CCH_2OCOCH_3$, $R_5$ and $R_6$ are H independently; or $R_3$ is H, $R_4$ is Cl, $R_5$ and $R_6$ are H independently; or $R_3$ is H, $R_4$ is $C\equiv CSi(CH_3)_3$, $R_5$ and $R_6$ are H independently; or $R_3$ is H, $R_4$ is $C\equiv C(CH_2)_nCH_3$ (n being an integer from 1 to 16), $R_5$ and $R_6$ are H independently; or $R_3$ is H, $R_4$ is $C\equiv CC_6H_5$, $R_5$ and $R_6$ are H independently; or $R_3$, $R_5$ and $R_6$ are $C(CH_3)_3$ independently, and $R_4$ is Cl; or $R_3$, $R_5$ and $R_6$ are $C(CH_3)_3$ independently, and $R_4$ is $C\equiv CC_6H_5$.

Wherein said 6-phenyl-2,2'-bipyridyl platinum(II) complex has the following structure represented by Formula III:

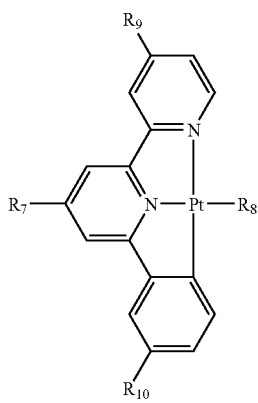

Formula III wherein in Formula III, $R_7$ is H, $R_8$ is Cl, $R_9$ and $R_{10}$ are H independently; or $R_7$ is $C_6H_5$, $R_8$ is Cl, $R_9$ and $R_{10}$ are H independently; or $R_7$ is $C_6H_4CH_3$-4, $R_8$ is $C\equiv CC_6H_4CH_3$-4, $R_9$ and $R_{10}$ are H independently; or $R_7$ is $C_6H_4CH_3$-4, $R_8$ is Cl, $R_9$ and $R_{10}$ are H independently; or $R_7$ is $C_6H_4CH_3$-4, $R_8$ is $C\equiv CC_6H_4C\equiv CC_6H_5$-4, $R_9$ and $R_{10}$ are H independently; or $R_7$ is $C_6H_4OCH_3$-4, $R_8$ is Cl, $R_9$ and $R_{10}$ are H independently; or $R_7$ is $C_6H_4OCH_3$-4, $R_8$ is $C\equiv CC_6H_4C\equiv CC_6H_5$-4, $R_9$ and $R_{10}$ are H independently; or $R_7$ is $C_6H_4OCH_3$-4, $R_8$ is $C\equiv CC_6H_5$, $R_9$ and $R_{10}$ are H independently; or $R_7$ is $C_6H_4CH_3$-4, $R_8$ is $C\equiv CC_6H_5$, $R_9$ and $R_{10}$ are H independently; or $R_7$ is $C_6H_4CH_3$-4, $R_8$ is $C\equiv CC_6H_4Cl$-4, $R_9$ and $R_{10}$ are H independently.

Wherein said 2,2'-bipyridyl platinum(II) complex has the following structure represented by Formula IV:

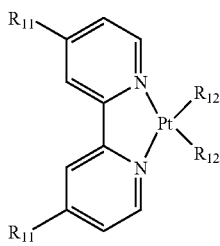

Formula IV wherein in Formula IV, $R_{11}$ is H, $CH_3$, Cl, $OCH_3$ or $C(CH_3)_3$; $R_{12}$ is Cl, $C\equiv CC_6H_4CH_3$-4, $C\equiv CC_6H_4C\equiv CC_6H_5$-4, $C\equiv CCH_2OH$, $C\equiv CC_6H_5$, $C\equiv CC_6H_4OCH_3$-4, $C\equiv CC_6H_4OCOCH_3$, $C\equiv CSi(CH_3)_3$ or $C\equiv C(CH_2)_nCH_3$ (n being an integer from 1 to 16).

Wherein said phenanthroline platinum(II) complex has the following structure represented by Formula V:

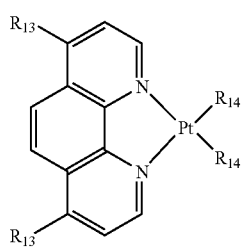

Formula V wherein in Formula V, $R_{13}$ is H or $CH_3$; $R_{14}$ is Cl, $C\equiv CC_6H_4CH_3$-4, $C\equiv CC_6H_4C\equiv CC_6H_5$-4, $C\equiv CCH_2OH$, $C\equiv CC_6H_5$, $C\equiv CC_6H_4OCH_3$-4, $C\equiv CC_6H_4OCOCH_3$, $C\equiv CSi(CH_3)_3$ or $C\equiv C(CH_2)_nCH_3$ (n being an integer from 1 to 16).

The present invention using polypyridyl platinum (II) complex and visible light is to provide highly efficient isomerization of 1,2-diphenylethylene analogues. In view of the specific properties of polypyridyl platinum (II) complex, the cis-1,2-diphenylethylene analogue or cis-1,2-diphenylethylene analogue obtained as a predominant product can be easily separated with the catalyst. And the catalyst can be recycled.

EXAMPLES

The present invention is explained in more detail by means of the following examples, which, however, are not intended to be construed as restricting the scope of the present invention.

Example 1

Using 2,2':6',2"-terpyridyl platinum(II) complex (wherein $R_3$ is $C_6H_4OCH_3$-4, $R_4$ is $C\equiv CC_6H_4C\equiv CC_6H_5$-4, $R_5$ and $R_6$ are H independently) as catalyst, 1,2-diphenylethylene (wherein $R_1$ is a phenyl, $R_2$ is a phenyl) as the substance dissolved in acetonitrile, using a 500 W high pressure mercury lamp with a 400 nm glass optical filter to irradiate the acetonitrile solution.

Into the transparent glass reactor containing 3.60 mg trans-1,2-diphenylethylene (wherein $R_1$ is a phenyl, $R_2$ is a phenyl) in 20 mL acetonitrile with concentration of $1\times10^{-3}$ mol/L, 2,2':6',2"-terpyridyl platinum(II) complex (wherein $R_3$ is $C_6H_4OCH_3$-4, $R_4$ is $C\equiv CC_6H_4C\equiv CC_6H_5$-4, $R_5$ and $R_6$ are H independently) was added with concentration of $1\times10^{-5}$ mol/L. Under the argon or nitrogen atmosphere, irradiation was carried out for 10 min with the 400 nm glass optical filter, monitored by UV-vis spectroscopy. The spectral changes of reaction solution are shown in FIG. 1. The detection of GC indicated that 90% of trans-1,2-diphenylethylene (wherein $R_1$ is phenyl, $R_2$ is phenyl) isomerized to cis-1,2-diphenylethylene (wherein $R_1$ is phenyl, $R_2$ is phenyl) after the irradiation. At the end of the reaction the solvent was evaporated and then $CH_3COOEt$ was added, followed by extraction and filtration. The catalyst was separated and recycled by filtration, and the filtrate of $CH_3COOEt$ was subject to the product analysis and purification to provide the expected product(s).

Example 2

Using 2,2':6',2"-terpyridyl platinum(II) complex (wherein $R_3$ is $C_6H_4OCH_3$-4, $R_4$ is $C\equiv CC_6H_4C\equiv CC_6H_5$-4, $R_5$ and $R_6$ are H independently) as catalyst, trans-4-pyridyl styrene (wherein $R_1$ is phenyl, $R_2$ is 4-pyridyl) as the substance dissolved in deuterium acetonitrile, using a 500 W high pressure mercury lamp with a 400 nm glass optical filter to irradiate the deuterium acetonitrile solution.

Figure 2:
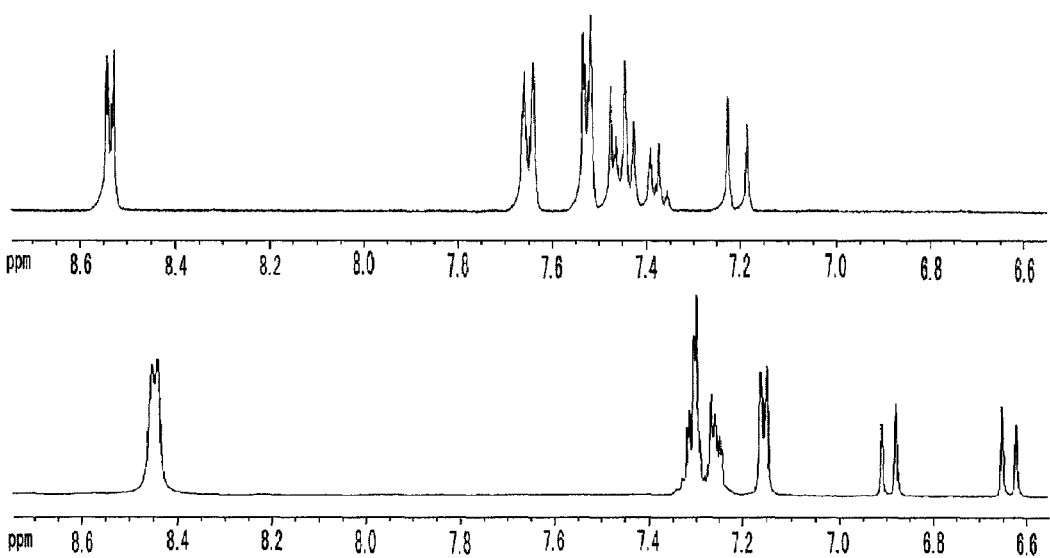
FIG. 2 shows the $^1$H NMR spectra of the solution before (a) and after (b) the irradiation containing trans-4-pyridyl styrene (wherein $R_1$ is phenyl, $R_2$ is pyridyl) and 2,2':6',2''-terpyridyl platinum(II) complex (wherein $R_3$ is $C_6H_4OCH_3$-4, $R_4$ is $C\equiv CC_6H_4C\equiv CC_6H_5$-4, $R_5$ and $R_6$ are H independently) in deuterium acetonitrile in example 2.

Into the solution of 0.6 mL deuterium acetonitrile containing 2,2':6',2"-terpyridyl platinum(II) complex (wherein $R_3$ is $C_6H_4OCH_3$-4, $R_4$ is $C\equiv CC_6H_4C\equiv CC_6H_5$-4, $R_5$ and $R_6$ are H independently) with concentration of $1\times10^{-5}$ mol/L, 1.0 mg trans-4-pyridyl styrene (wherein $R_1$ is phenyl, $R_2$ is 4-pyridyl) with concentration of $1\times10^{-2}$ mol/L was added. Under the nitrogen atmosphere the irradiation was carried out with the 500 W high-pressure mercury lamp and the 400 nm glass optical filter for 30 min. The changes of $^1$H NMR spectrum before and after the irradiation are shown in FIG. 2. It is evident that almost all of the trans-4-pyridyl styrene (wherein $R_1$ is phenyl, $R_2$ is 4-pyridy) isomerized to cis-4-pyridyl styrene (wherein $R_1$ is phenyl, $R_2$ is 4-pyridy) after the irradiation. At the end of the reaction the solvent was evaporated and then $CH_3COOEt$ was added followed by extraction and filtration. The catalyst was separated and recycled by filtration, and the filtrate of $CH_3COOEt$ was subject to the product analysis and purification to provide the expected product(s).

Example 3

Using 6-phenyl-2,2'-bipyridyl platinum(II) complex (wherein $R_7$ is $C_6H_4CH_3$-4, $R_8$ is $C\equiv CC_6H_4C\equiv CC_6H_5$-4, $R_9$ and $R_{10}$ are H independently) as catalyst, trans-1,2-diphenylethylene (wherein $R_1$ is phenyl, $R_2$ is phenyl) as the substance dissolved in benzene, using a 500 W high pressure mercury lamp with a 350 nm glass optical filter to irradiate the benzene solution.

Under the nitrogen atmosphere and into the transparent glass reactor containing 1.80 mg trans-1,2-diphenylethylene (wherein $R_1$ is phenyl, $R_2$ is phenyl) with concentration of $1.0\times 10^{-3}$ mol/L in 10 mL benzene solution, 6-phenyl-2,2'-bipyridyl platinum(II) complex (wherein $R_7$ is $C_6H_4CH_3$-4, $R_8$ is $C\equiv CC_6H_4C\equiv CC_6H_5$-4, $R_9$ and $R_{10}$ are H independently) was added with concentration of $1.0\times 10^{-5}$ mol/L. The irradiation was carried out for 30 min with the 350 nm glass optical filter, monitored by GC. The detection of GC indicated that 83% of trans-1,2-diphenylethylene (wherein $R_1$ is phenyl, $R_2$ is phenyl) isomerized to cis-1,2-diphenylethylene (wherein $R_1$ is phenyl, $R_2$ is phenyl) after the irradiation. At the end of the reaction the solvent was evaporated and then $CH_3COOEt$ was added followed by extraction and filtration. The catalyst was separated and recycled by filtration, and the filtrate of $CH_3COOEt$ was subject to the product analysis and purification to provide the expected product(s).

Example 4

Using phenanthroline platinum(II) complex (wherein $R_{13}$ is H, $R_{14}$ is Cl) as catalyst, trans-1,2-diphenylethylene (wherein $R_1$ is phenyl, $R_2$ is phenyl) as the substance dissolved in acetonitrile, using a 500 W high pressure mercury lamp with a 350 nm glass optical filter to acetonitrile solution.

Under the nitrogen atmosphere and into the transparent glass reactor containing 7.2 mg trans-1,2-diphenylethylene (wherein $R_1$ is phenyl, $R_2$ is phenyl) with concentration of $2.0\times 10^{-3}$ mol/L in 20 mL acetonitrile solution, phenanthroline platinum(II) complex (wherein $R_{13}$ is H, $R_{14}$ is Cl) was added with concentration of $1.0\times 10^{-5}$ mol/L. The irradiation was carried out for 1 h with the 350 nm glass optical filter, monitored by GC. The detection of GC indicated that 67% of trans-1,2-diphenylethylene (wherein $R_1$ is phenyl, $R_2$ is phenyl) isomerized to cis-1,2-diphenylethylene (wherein $R_1$ is phenyl, $R_2$ is phenyl) after the irradiation. At the end of the reaction the solvent was evaporated and then $CH_3COOEt$ was added followed by extraction and filtration. The catalyst was separated and recycled by filtration, and the filtrate of $CH_3COOEt$ was subject to the product analysis and purification to provide the expected product(s).

Example 5

Using 2,2':6',2''-terpyridyl platinum(II) complex (wherein $R_3$ is $C_6H_4CH_3$-4, $R_4$ is $C\equiv C(CH_2)_2CH_3$, $R_5$ and $R_6$ are H independently) as catalyst, trans-2-naphthyl ethylene pyridine (wherein $R_1$ is 4-pyridyl, $R_2$ is 2-naphthyl) as the substance dissolved in acetonitrile, using a 500 W high pressure mercury lamp with a 400 nm glass optical filter to irradiate the acetonitrile solution.

Under the nitrogen atmosphere and into the transparent glass reactor containing 4.62 mg trans-2-naphthylethylene pyridine (wherein $R_1$ is 4-pyridyl, $R_2$ is 2-naphthyl) with concentration of $1.0\times 10^{-3}$ mol/L in 20 mL acetonitrile solution, 2,2':6',2''-terpyridyl platinum(II) complex (wherein $R_3$ is $C_6H_4CH_3$-4, $R_4$ is $C\equiv C(CH_2)_2CH_3$, $R_5$ and $R_6$ are H independently) was added with concentration of $1.0\times 10^{-5}$ mol/L. Irradiation was carried out for 1 h with the 350 nm glass optical filter, monitored by GC. The detection of GC indicated that 63% of trans-2-naphthylethylene pyridine (wherein $R_1$ is 4-pyridyl, $R_2$ is 2-naphthyl) isomerized to cis-2-naphthylethylene pyridine (wherein $R_1$ is 4-pyridyl, $R_2$ is 2-naphthyl) after the irradiation. At the end of the reaction the solvent was evaporated and then $CH_3COOEt$ was added followed by extraction and filtration. The catalyst was separated and recycled by filtration, and the filtrate of $CH_3COOEt$ was subject to the product analysis and purification to provide the expected product(s).

Example 6

Using 2,2':6',2''-terpyridyl platinum(II) complex (wherein $R_3$ is $C_6H_4CH_3$-4, $R_4$ is $C\equiv CC_6H_4CH_3$-4, $R_5$, $R_6$ are H independently) as catalyst, a mixture of trans-1,2-diphenylethylene and cis-1,2-diphenylethylene (wherein $R_1$ is phenyl, $R_2$ is phenyl) as the substance dissolved in acetonitrile, using a 500 W high pressure mercury lamp with a 400 nm glass optical filter to irradiate the acetonitrile solution.

Under the argon or nitrogen atmosphere and into the transparent glass reactor containing 1.80 mg trans-1,2-diphenylethylene (wherein $R_1$ is phenyl, $R_2$ is phenyl) and 1.80 mg cis-1,2-diphenylethylene (wherein $R_1$ is phenyl, $R_2$ is phenyl) with total concentration of $1.0\times 10^{-3}$ mol/L in 20 mL acetonitrile solution (the concentration of trans-1,2-diphenylethylene and cis-1,2-diphenylethylene is $5.0\times 10^{-4}$ mol/L, respectively), 2,2':6',2''-terpyridyl platinum(II) complex (wherein $R_3$ is $C_6H_4CH_3$-4, $R_4$ is $C\equiv CC_6H_4CH_3$-4, $R_5$, $R_6$ are H independently) was added with concentration of $1.0\times 10^{-5}$ mol/L. Irradiation was carried out with the 400 nm glass optical filter, monitored by GC. The detection of GC indicated that there was 94% cis-1,2-diphenylethylene (wherein $R_1$ is phenyl, $R_2$ is phenyl) in the reaction system after the irradiation. At the end of the reaction the solvent was evaporated and then $CH_3COOEt$ was added followed by extraction and filtration. The catalyst was separated and recycled by filtration, and the filtrate of $CH_3COOEt$ was subject to the product analysis and purification to provide the expected product(s).

We claim:

1. A method for photocatalytic isomerization of 1,2-diphenylethylene analogues, wherein in the presence of catalyst of polypyridyl platinum(II) complex with catalytic dosage, a solution containing trans-1,2-diphenylethylene analogues or mixture of cis- and trans-1,2-diphenylethylene analogues is irradiated by visible light under inert gas atmosphere to prepare product of cis-1,2-diphenylethylene analogues or product predominantly being cis-1,2-diphenylethylene analogues.

2. The method according to claim 1, wherein the concentration of the polypyridyl platinum (II) complex in the solution is from about $10^{-7}$ mol/L to saturation.

3. The method according to claim 1, wherein the concentration of the trans-1,2-diphenylethylene analogues or the mixture of cis- and trans-1,2-diphenylethylene analogues in the solution is from about $10^{-5}$ mol/l to saturation.

4. The method according to claim 1, wherein the solvent of the solution is one or more selected from the group consisting of acetonitrile, dichloromethane, benzene, and toluene.

5. The method according to claim 1, wherein the wavelength of the visible light is about 350 nm or longer.

6. The method according to claim 1, wherein the trans-1,2-diphenylethylene analogues has the following structure represented by Formula I(a):

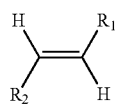

Formula I (a)

the cis-1,2-diphenylethylene analogues has the following structure represented by Formula I(b):

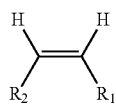

Formula I (b)

wherein in Formula I, $R_1$ is phenyl, and $R_2$ is phenyl, 2-pyridyl, 3-pyridyl, 4-pyridyl, 2-furyl, 4-methylphenyl, 4-methoxylphenyl or 4-nitrophenyl; or $R_1$ is 2-thienyl, and $R_2$ is 2-thienyl, phenyl, 4-methylphenyl, or 4-methoxylphenyl; or $R_1$ is 3-thienyl, and $R_2$ is phenyl, 4-methylphenyl, or 4-methoxylphenyl; or $R_1$ is 2-pyridyl, and $R_2$ is 2-pyridyl, 4-pyridyl, 4-methylphenyl, 4-methoxylphenyl or 2-naphthyl; or $R_1$ is 4-pyridyl, and $R_2$ is 4-pyridyl, 4-methylphenyl, 4-methoxylphenyl or 2-naphthyl; or $R_1$ and $R_2$ each are independently selected from 4-methylphenyl and 4-methoxylphenyl independently.

7. The method according to claim 1, wherein the catalyst of the polypyridyl platinum(II) complex is 2,2':6',2''-terpyridyl platinum(II) complex, 6-phenyl-2,2'-bipyridyl platinum(II) complex, 2,2'-bipyridyl platinum(II) complex or phenanthroline platinum(II) complex.

8. The method according to claim 7, wherein the 2,2':6',2''-terpyridyl platinum(II) complex has the structure represented by Formula II:

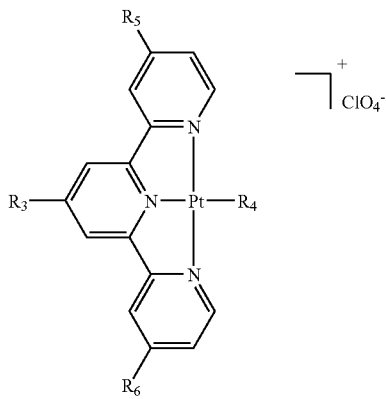

Formula II wherein in Formula II, $R_3$ is $C_6H_4OCH_3$-4, $R_4$ is $C\equiv CC_6H_4C\equiv CC_6H_5$-4, $R_5$ and $R_6$ are H independently; or $R_3$ is $C_6H_4OCH_3$-4, $R_4$ is Cl, $R_5$ and $R_6$ are H independently; or $R_3$ is $C_6H_4CH_3$-4, $R_4$ is $C\equiv CC_6H_4C\equiv CC_6H_5$-4, $R_5$, $R_6$ are H independently; or $R_3$ is $C_6H_4CH_3$-4, $R_4$ is Cl, $R_5$ and $R_6$ are H independently; or $R_3$ is $C_6H_4CH_3$-4, $R_4$ is $C\equiv CC_6H_4CH_3$-4, $R_5$ and $R_6$ are H independently; or $R_3$ is $C_6H_4CH_3$-4, $R_4$ is $C\equiv CCH_2OH$, $R_5$ and $R_6$ are H independently; or $R_3$ is $C(CH_3)_3$, $R_4$ is $C\equiv CC_6H_5$, $R_5$ and $R_6$ are H independently; or $R_3$ is $C(CH_3)_3$, $R_4$ is Cl, $R_5$ and $R_6$ are H independently; or $R_3$ is $C_6H_4CH_3$-4, $R_4$ is $C\equiv CC_6H_5$, $R_5$ and $R_6$ are H independently; or $R_3$ is $C_6H_4CH_3$-4, $R_4$ is $C\equiv CC_6H_4OCH_3$-4, $R_5$ and $R_6$ are H independently; or $R_3$ is $C_6H_4CH_3$-4, $R_4$ is $C\equiv CC_6H_4Cl$-4, $R_5$ and $R_6$ are H independently; or $R_3$ is $C_6H_4CH_3$-4, $R_4$ is $C\equiv CC_6H_4OCOCH_3$, $R_5$ and $R_6$ are H independently; or $R_3$ is $C_6H_4CH_3$-4, $R_4$ is $C\equiv CSi(CH_3)_3$, $R_5$ and $R_6$ are H independently; or $R_3$ is $C_6H_4CH_3$-4, $R_4$ is $C\equiv C(CH_2)_nCH_3$ (n being an integer from 1 to 16), $R_5$ and $R_6$ are H independently; or $R_3$ is H, $R_4$ is $C\equiv CCH_2OCOCH_3$, $R_5$ and $R_6$ are H independently; or $R_3$ is H, $R_4$ is Cl, $R_5$ and $R_6$ are H independently; or $R_3$ is H, $R_4$ is $C\equiv CSi(CH_3)_3$, $R_5$ and $R_6$ are H independently; or $R_3$ is H, $R_4$ is $C\equiv C(CH_2)_nCH_3$ (n being an integer from 1 to 16), $R_5$ and $R_6$ are H independently; or $R_3$ is H, $R_4$ is $C\equiv CC_6H_5$, $R_5$ and $R_6$ are H independently; or $R_3$, $R_5$ and $R_6$ are $C(CH_3)_3$ independently, and $R_4$ is Cl; or $R_3$, $R_5$ and $R_6$ are $C(CH_3)_3$ independently, and $R_4$ is $C\equiv CC_6H_5$;

wherein said 6-phenyl-2,2'-bipyridyl platinum(II) complex has the following structure represented by Formula III:

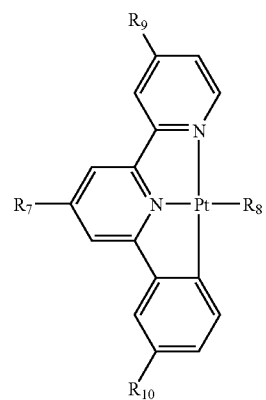

Formula III wherein in Formula III, $R_7$ is H, $R_8$ is Cl, $R_9$ and $R_{10}$ are H independently; or $R_7$ is $C_6H_5$, $R_8$ is Cl, $R_9$ and $R_{10}$ are H independently; or $R_7$ is $C_6H_4CH_3$-4, $R_8$ is $C\equiv CC_6H_4CH_3$-4, $R_9$ and $R_{10}$ are H independently; or $R_7$ is $C_6H_4CH_3$-4, $R_8$ is Cl, $R_9$ and $R_{10}$ are H independently; or $R_7$ is $C_6H_4CH_3$-4, $R_8$ is $C\equiv CC_6H_4C\equiv CC_6H_5$-4, $R_9$ and $R_{10}$ are H independently; or $R_7$ is $C_6H_4OCH_3$-4, $R_8$ is Cl, $R_9$ and $R_{10}$ are H independently; or $R_7$ is $C_6H_4OCH_3$-4, $R_8$ is $C\equiv CC_6H_4C\equiv CC_6H_5$-4, $R_9$ and $R_{10}$ are H independently; or $R_7$ is $C_6H_4OCH_3$-4, $R_8$ is $C\equiv CC_6H_5$, $R_9$ and $R_{10}$ are H independently; or $R_7$ is $C_6H_4CH_3$-4, $R_8$ is $C\equiv CC_6H_5$, $R_9$ and $R_{10}$ are H independently; or $R_7$ is $C_6H_4CH_3$-4, $R_8$ is $C\equiv CC_6H_4Cl$-4, $R_9$ and $R_{10}$ are H independently;

wherein said 2,2'-bipyridyl platinum(II) complex has the following structure represented by Formula IV:

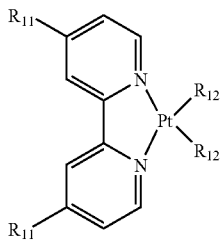

Formula IV

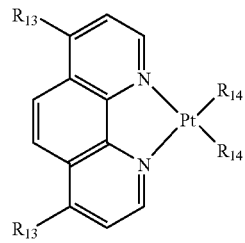

Formula V wherein in Formula IV, $R_{11}$ is H, $CH_3$, Cl, $OCH_3$ or $C(CH_3)_3$; $R_{12}$ is Cl, $C{\equiv}CC_6H_4CH_3$-4, $C{\equiv}CC_6H_4C{\equiv}CC_6H_5$-4, $C{\equiv}CCH_2OH$, $C{\equiv}CC_6H_5$, $C{\equiv}CC_6H_4OCH_3$-4, $C{\equiv}CC_6H_4OCOCH_3$, $C{\equiv}CSi(CH_3)_3$ or $C{\equiv}C(CH_2)_nCH_3$ (n being an integer from 1 to 16);

wherein said phenanthroline platinum(II) complex has the following structure represented by Formula V:

wherein in Formula V, $R_{13}$ is H or $CH_3$; $R_{14}$ is Cl, $C{\equiv}CC_6H_4CH_3$-4, $C{\equiv}CC_6H_4C{\equiv}CC_6H_5$-4, $C{\equiv}CCH_2OH$, $C{\equiv}CC_6H_5$, $C{\equiv}CC_6H_4OCH_3$-4, $C{\equiv}CC_6H_4OCOCH_3$, $C{\equiv}CSi(CH_3)_3$ or $C{\equiv}C(CH_2)_nCH_3$ (n being an integer from 1 to 16).

* * * * *